(12) United States Patent
Qu et al.

(10) Patent No.: US 11,946,684 B2
(45) Date of Patent: Apr. 2, 2024

(54) SPIRALLY ASCENDING/DESCENDING CRYOGENIC STORAGE APPARATUS (71) Applicant: SHANGHAI ORIGINCELL BIOLOGICAL CRYO EQUIPMENT CO., LTD., Shanghai (CN)

(72) Inventors: Jianguo Qu, Shanghai (CN); Chen Luo, Shanghai (CN); Jianxin Wang, Shanghai (CN)

(73) Assignee: SHANGHAI ORIGINCELL BIOLOGICAL CRYO EQUIPMENT CO., LTD., Shanghai (CN)

( * ) Notice: Subject to any disclaimer, the term of this patent is extended or adjusted under 35 U.S.C. 154(b) by 563 days.

(21) Appl. No.: 17/276,975

(22) PCT Filed: Jan. 4, 2019

(86) PCT No.: PCT/CN2019/070360
§ 371 (c)(1),
(2) Date: May 18, 2021

(87) PCT Pub. No.: WO2020/057015
PCT Pub. Date: Mar. 26, 2020

(65) Prior Publication Data
US 2022/0026135 A1 Jan. 27, 2022

(30) Foreign Application Priority Data
Sep. 17, 2018 (CN) .......................... 201811080517.0

(51) Int. Cl.
F25D 13/06 (2006.01)
A01N 1/02 (2006.01)
(Continued)

(52) U.S. Cl.
CPC ........... *F25D 13/062* (2013.01); *F25D 23/02* (2013.01); *F25D 25/027* (2013.01); *A01N 1/0257* (2013.01); *F25D 2323/00* (2013.01)

(58) Field of Classification Search
CPC ...... F25D 13/062; F25D 23/02; F25D 25/027; F25D 2323/00; A01N 1/0257
See application file for complete search history.

(56) References Cited

U.S. PATENT DOCUMENTS 5,233,844 A 8/1993 Knippscheer et al.
6,475,776 B1 11/2002 Higuchi
(Continued)

FOREIGN PATENT DOCUMENTS

CN 203865247 U 10/2014
CN 204259702 U 4/2015
(Continued)

OTHER PUBLICATIONS

Chinese Office Action for Chinese Counterpart Application No. 201811080517.0, dated Apr. 27, 2023 (6 pages).
(Continued)

*Primary Examiner* — Nelson J Nieves
(74) *Attorney, Agent, or Firm* — Kagan Binder, PLLC (57) ABSTRACT A spirally ascending/descending cryogenic storage apparatus, comprising a cryogenic storage tank, the temperature in the cryogenic storage tank being continuously maintained at a certain deep cryogenic range. A driving component and a rotating storage rack are provided within the cryogenic storage tank. Multiple shelf boxes can be stored in the circumferential direction of the rotating storage rack. The driving component can drive the rotating storage rack to spirally ascent or spirally descent in the cryogenic storage tank. An access opening is provided on the cryogenic storage tank. The multiple shelf boxes can rotate to a position
(Continued)

corresponding to the access opening with the movement of the rotating storage rack. The cryogenic storage tank is a liquid nitrogen tank. Liquid nitrogen is provided at the bottom part within the liquid nitrogen tank.

13 Claims, 7 Drawing Sheets

(51) Int. Cl.
     *F25D 23/02*      (2006.01)
     *F25D 25/02*      (2006.01)

(56) References Cited

U.S. PATENT DOCUMENTS

| | | | |
|---|---|---|---|
| 9,005,542 B2* | 4/2015 | Malin | G01N 35/028 |
| | | | 414/788.1 |
| 9,174,790 B2* | 11/2015 | Malin | A01N 1/0257 |
| 9,835,640 B2* | 12/2017 | Raicu | B65G 1/06 |
| 9,926,525 B2* | 3/2018 | Norey | C12M 27/02 |
| 10,336,539 B2* | 7/2019 | Caveney | F25D 29/001 |
| 10,617,116 B2* | 4/2020 | Aota | C12M 1/00 |
| 2012/0134897 A1 | 5/2012 | Malin | |
| 2012/0134898 A1 | 5/2012 | Malin | |
| 2014/0190977 A1 | 7/2014 | Malin | |
| 2018/0202908 A1 | 7/2018 | Croquette et al. | |

FOREIGN PATENT DOCUMENTS

| | | |
|---|---|---|
| CN | 105857932 A | 8/2016 |
| CN | 105857937 A | 8/2016 |
| CN | 105857941 A | 8/2016 |
| CN | 205854983 U | 1/2017 |
| CN | 108045765 A | 5/2018 |
| CN | 108045766 A | 5/2018 |
| CN | 208987622 U | 6/2019 |
| DE | 102004053170 A1 | 5/2006 |
| EP | 0588068 A1 | 3/1994 |
| EP | 2492663 A2 | 8/2012 |

OTHER PUBLICATIONS

International Search Report, and English Translation thereof, for International Application No. PCT/CN2019/070360, dated Jun. 12, 2019 (6 pages).

Extended European Search Report for European Counterpart Application No. 19863867.8, dated May 25, 2022 (5 pages).

* cited by examiner

SPIRALLY ASCENDING/DESCENDING CRYOGENIC STORAGE APPARATUS

TECHNICAL FIELD

The present disclosure relates to the field of cryogenic storage, and more particularly to a spirally ascending/descending cryogenic storage apparatus.

BACKGROUND

The deep cryogenic biological sample bank currently is an important basic equipment for research in the field of medicine and biology. Biological tissues such as blood, stem cells, immune cells, and the like can maintain activity for a long time through cryopreservation. At present, the common cryogenic storage equipment is a liquid nitrogen storage tank with a manual structure. When an operator needs to retrieve a cryopreservation tube, the operator needs to open a tank cover, and reaches into a tank body to take out an entire cryopreservation tray before picking out a single cryopreservation tube, and in a process of storing the cryopreservation tube, the access action of the cryopreservation tube needs to be carried out after the tank cover of the liquid nitrogen tank is opened. This access method makes the entire cryopreservation tube or a cryopreservation box exposed to an environment with a temperature of more than −196° C., so that the biological performance of the cells stored in the other cryopreservation tubes will be affected, and the activity of the cells will be damaged, thus failing to meet the technical requirements for cell storage. Taking the existing patent CN205854983U as an example, a main body of a cryogenic storage platform is provided, and a sample is disposed in a refrigeration box in the cryogenic storage platform. When the sample needs to be retrieved, the entire refrigeration box needs to be opened, and then the refrigeration box is closed after the sample is found and taken out. In this way, during the sample retrieval process, the entire box of samples will be exposed at room temperature, which affects the preservation of the samples. It cannot be guaranteed that the entire cryopreservation tube or the cryopreservation box will be exposed to a temperature below −196° C., which will affect the biological performance of the cells stored in the remaining cryopreservation tubes, the activity of the cells will be damaged, and thus failing to meet the technical requirements for cell storage.

Although there are also technical solutions for improvement in the prior art, for example, in the existing patent EP2492663A2, a plurality of fan-shaped baskets are provided at the top of a liquid nitrogen tank, and each basket is provided with a plurality of cryopreservation trays, and the cryopreservation trays are provided with cryopreservation tubes. A closed transition chamber is provided above the liquid nitrogen tank. When it is necessary to store or retrieve cryopreservation tubes, the entire basket needs to be retrieved into the closed transition chamber, and then the cryopreservation tray is taken out. Although the closed transition chamber is provided, the closed transition chamber is provided above the liquid nitrogen tank, the entire closed transition chamber needs to be refrigerated at the same time, the space that requires liquid nitrogen refrigeration is greatly increased, and the refrigeration performance of the closed transition chamber cannot be guaranteed. In addition, a large amount of liquid nitrogen is consumed for each access, and since the entire basket is first retrieved into the closed transition chamber, samples of the cryopreservation tubes on the entire basket are affected. Therefore, the cryogenic storage apparatus in the prior art has the problems of large volume, small storage capacity, large nitrogen consumption, inconvenient operation, and low retrieval rate. Therefore, the method of operation increases the safety hazard to the storage or retrieval of the cryopreservation box, and affects the storage efficiency of the cryopreservation box.

SUMMARY

The present disclosure aims to provide a spirally ascending/descending cryogenic storage apparatus, which solves the problems that a cryogenic storage apparatus in the prior art has the safety hazard of damaging the cell activity during the retrieval process, and is large in size, small in storage capacity and inconvenient in operation.

The present disclosure solves the technical problem by adopting the following technical solutions: a spirally ascending/descending cryogenic storage apparatus includes a cryogenic storage tank. A temperature in the cryogenic storage tank is continuously maintained in a certain deep cryogenic range. The cryogenic storage tank is provided with a drive assembly and a rotating storage rack therein. The rotating storage rack is capable of storing a plurality of shelf boxes in a circumferential direction. The drive assembly is capable of driving the rotating storage rack to spirally ascend or spirally descend in the cryogenic storage tank. The cryogenic storage tank is provided with an access opening, and the plurality of shelf boxes is capable of moving to a position corresponding to the access opening along with a movement of the rotating storage rack.

Preferably, the cryogenic storage tank is a liquid nitrogen tank, and liquid nitrogen is provided at a bottom in the liquid nitrogen tank.

Preferably, a storage housing is further included. The cryogenic storage tank is disposed inside the storage housing, the storage housing is provided with an access door, and the access door corresponds to the access opening.

Preferably, the drive assembly includes a drive motor, a transition gear assembly, and a drive shaft assembly. The drive motor is connected to the transition gear assembly, the transition gear assembly is connected to the drive shaft assembly, and the drive motor is capable of driving the drive shaft assembly to rotate through the transition gear assembly. The rotating storage rack is provided with an operation channel extending through from top to bottom at a center of a circumference thereof. The drive shaft assembly acts in the operation channel, and the drive shaft assembly is provided with a drive connecting unit, and a drive receiving unit is provided in the operation channel. The drive shaft assembly is capable of driving the rotating storage rack to rotate through the drive connecting unit acting on the drive receiving unit.

Preferably, the drive shaft assembly includes a lead screw and a rotation shaft sleeve. The transition gear assembly is connected to the rotation shaft sleeve. The rotation shaft sleeve is sleeved on a periphery of an upper half of the lead screw, and a lower end of the lead screw extends out of the rotation shaft sleeve. A periphery of a circumference of the rotation shaft sleeve extends outwards to form at least one guide ball, an inner wall of the operation channel of the rotating storage rack is recessed inwards to form at least one guide groove, and the guide ball extends into the guide groove. Under a cooperation of the guide ball and the guide groove, the rotation shaft sleeve is capable of driving the rotating storage rack to rotate in a circumferential direction. The operation channel of the rotating storage rack is fixedly provided with an inner nut seat at a lower end thereof. The lower end of the lead screw passes through the operation channel and is threadedly connected to the inner nut seat.

Preferably, there are three guide balls, and the guide balls are provided on the periphery of the rotation shaft sleeve in a circumferential array. The guide grooves are formed on the inner wall of the operation channel in an axial direction, and there are three guide grooves, the guide grooves are in one-to-one correspondence to the guide balls.

Preferably, the transition gear assembly includes a driving wheel and a driven wheel. The driving wheel is connected to a motor shaft of the drive motor, the driving wheel is in gear meshing connection with the driven wheel, and the driven wheel is fixedly disposed on a periphery of an upper end of the rotation shaft sleeve.

Preferably, the cryogenic storage tank further includes a tank body, an upper cover, and a sealing cover. The rotating storage rack is disposed in the tank body, the sealing cover is sealed on an upper end of the tank body, and the upper cover is covered on an upper end surface of the sealing cover. A fixed plate is fixedly provided under the sealing cover, a fixed disc is fixedly provided under the fixed plate. The driven wheel is disposed between the fixed plate and the fixed disc, and the driven wheel is in ball sliding connection with both the fixed plate and the fixed disc. The drive motor is disposed above the upper cover, and the motor shaft of the drive motor sequentially passes through the upper cover and the sealing cover and is connected to the driving wheel in the tank body.

Preferably, the rotating storage rack is provided by a plurality of rows of sub storage racks distributed in a circumferential direction, and each row of the sub storage racks is divided into a plurality of vertically arranged storage grooves by a plurality of resting plates; the shelf boxes are disposed in the storage grooves. The rotating storage rack is provided with a plurality of nitrogen introducing holes at an upper end surface and a lower end surface thereof, and each of the resting plates is provided with a nitrogen introducing hole.

Preferably, the storage grooves between two adjacent rows of the sub storage racks are staggered in an axial height, and the storage grooves forming the entire rotating storage rack are provided in a spiral arrangement.

Preferably, the storage housing is provided with an operation hole, the operation hole corresponds to the access opening;

a transition platform is fixed in the operation hole in an interference fit manner, the transition platform is provided with a transition access through hole, the transition access through hole is in communication with the access opening; the access door is disposed on a side of the transition platform away from the cryogenic storage tank.

Preferably, the transition platform is made of a thermal insulation material, and the thermal insulation material is polyisocyanurate foam (PIR), polyurethane resin (PUR), expanded polypropylene (EPP), expanded polystyrene (EPS), aerogel, or vacuum insulation board.

Optionally, a controller is further included. The controller is electrically connected to the drive assembly and controls the drive assembly.

Preferably, the access door further includes a controller, a door frame, an access hole, and a door. The door frame is provided with the controller at an upper part thereof, and the door frame is provided with the access hole at a lower part thereof. The access hole is in communication the access opening and the operation hole. The controller is electrically connected to the drive assembly, and controls the driving of the drive assembly.

The present disclosure has the following beneficial effects. The stability of the temperature during the retrieval of biological samples is ensured, the safety hazard of damaging cell activity is eliminated, and the internal ascending and descending rotation of the cryopreservation tubes in a limited space is achieved. The storage capacity is large, the operation is convenient, and the access rate of the cryopreservation tubes is greatly improved.

Reference numbers in the figures are as follows: 1—cryogenic storage tank; 2—drive assembly; 3—rotating storage rack; 4—shelf box; 5—access opening; 6—storage box base; 7—storage housing; 8—access door; 9—drive motor; 10—transition gear assembly; 11—drive shaft assembly; 12—operation channel; 13—drive connecting unit; 14—drive receiving unit; 15—lead screw; 16—rotation shaft sleeve; 17—guide ball; 18—guide groove; 19—inner nut seat; 20—driving wheel; 21—driven wheel; 22—tank body; 23—upper cover; 24—sealing cover; 25—fixed plate; 26—fixed disc; 27—sub storage rack; 28—resting plate; 29—storage groove; 30—nitrogen introducing hole; 31—first sub storage rack; 32—second sub storage rack; 33—operation hole; 34—transition platform; 35—transition access through hole; 36—controller; 37—door frame; 38—access hole; 39—door.

DETAILED DESCRIPTION OF THE EMBODIMENTS

The technical solutions of the present disclosure will be further described below with reference to embodiments and accompanying drawings.

Embodiment 1

Figure 1:
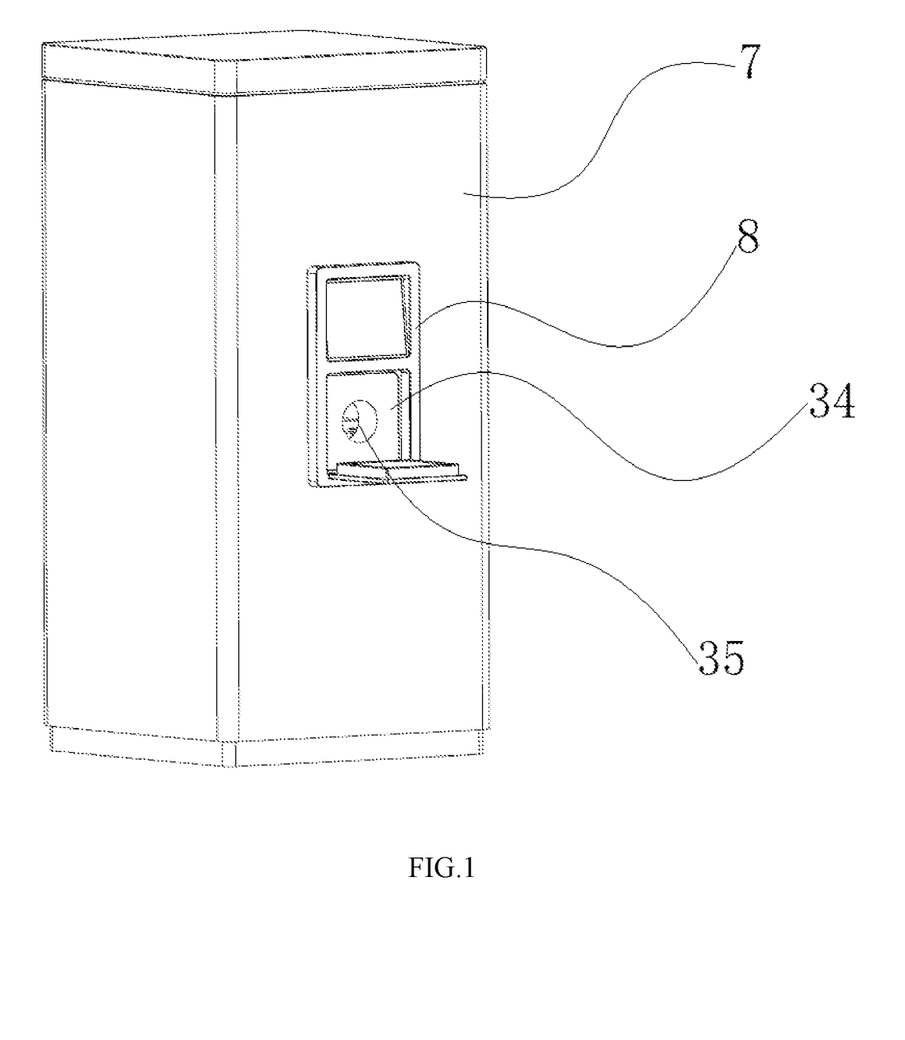
FIG. 1 is a schematic view of a spirally ascending/descending cryogenic storage apparatus.
Figure 2:
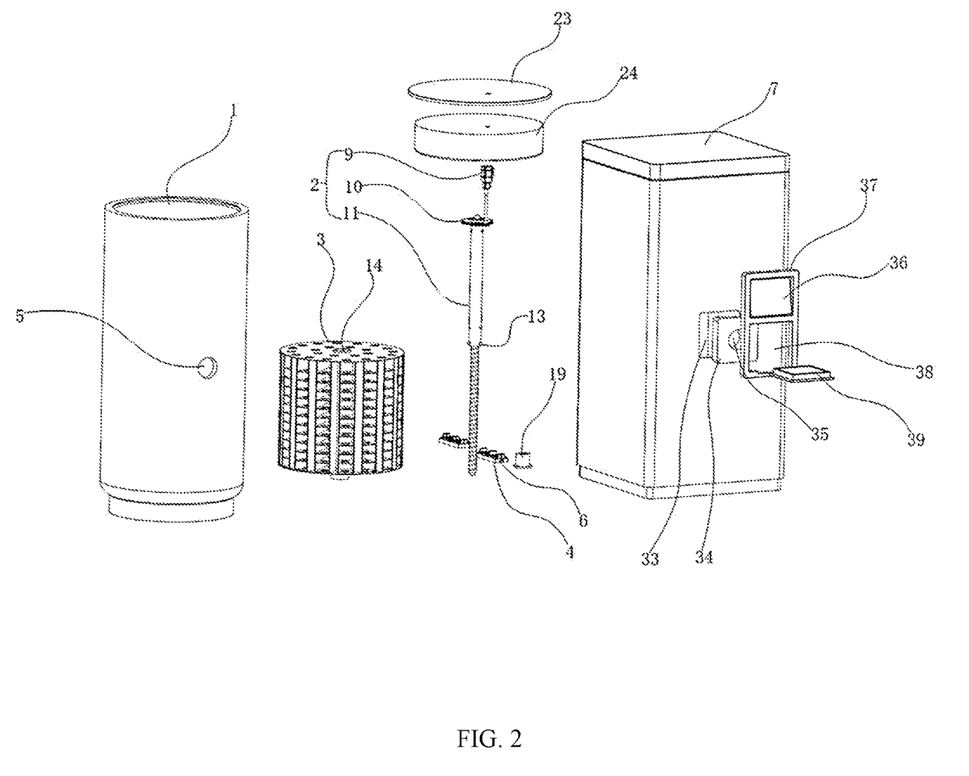
FIG. 2 is an exploded view of internal structures of a spirally ascending/descending cryogenic storage apparatus.
Figure 7:
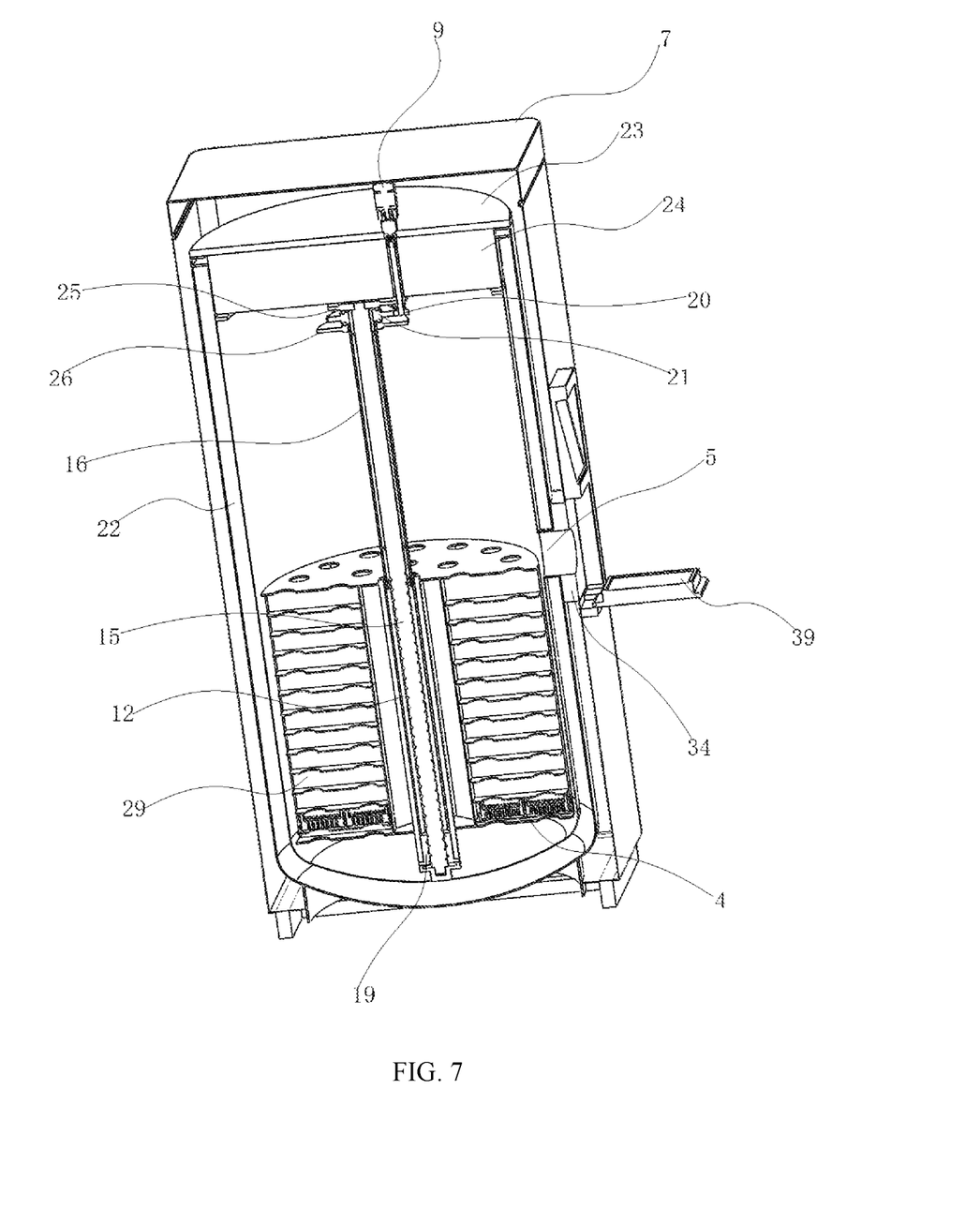
FIG. 7 is a half cross-sectional view of a spirally ascending/descending cryogenic storage apparatus.

This embodiment provides a spirally ascending/descending cryogenic storage apparatus, which includes a cryogenic storage tank 1. A temperature in the cryogenic storage tank 1 is continuously maintained within a certain deep cryogenic range. The cryogenic storage tank 1 is provided with a drive assembly 2 and a rotating storage rack 3 therein. The rotating storage rack 3 can store a plurality of shelf boxes 4 in a circumferential direction. The drive assembly 2 can drive the rotating storage rack 3 to spirally ascend or spirally descend in the cryogenic storage tank 1. The cryogenic storage tank 1 is provided with an access opening 5, the plurality of shelf boxes 4 can move to a position corresponding to the access opening 5 along with a movement of the rotating storage rack 3.

The shelf box 4 can be provided with a storage box base 6, and a cryopreservation tube is stored in the storage box base 6, and biological tissues that need to be preserved are stored in the cryopreservation tube. When the biological tissues need to be stored or retrieved, the drive assembly 2 is used to spirally ascend or spirally descend the rotating storage rack 3 in the cryogenic storage tank 1, so that the shelf box 4 that needs to be stored or retrieved moves to a position corresponding to the access opening 5, and thus the purpose of being able to store or retrieve biological tissue samples from the access opening 5 is achieved. In this way, it is not necessary to open the entire cryogenic storage tank 1, ensuring that all biological tissues in the cryopreservation tubes are kept in a deep cryogenic environment during storage or retrieval, which greatly improves the safety of biological tissue preservation. In addition, the rotating storage rack 3 spirally ascends or descends in the cryogenic storage tank 1, no additional conveying chamber or conveying channel is needed, the overall volume is small, the storage capacity is large, and the operation is convenient.

It is further described in detail in the following with the example of the cryogenic storage tank 1 being a liquid nitrogen tank, but not limited to a liquid nitrogen tank. The cryogenic storage tank 1 is a liquid nitrogen tank, and liquid nitrogen is arranged at the bottom within the liquid nitrogen tank.

In a preferred further implementation of the present embodiment, a storage housing 7 is further included. The cryogenic storage tank 1 is disposed inside the storage housing 7, and the storage housing 7 is provided with an access door 8, and the access door 8 corresponds to the access opening 5. The storage housing 7 is provided, so that the cryogenic storage tank 1 can be externally protected and heat insulated, which improves the working efficiency of the cryogenic storage tank 1. When biological tissues need to be stored or retrieved, the access door 8 is opened, and the access door 8 passes through the corresponding access opening 5 for storage or retrieval. Of course, this is not limited to the storage housing 7, but can also be a heat-insulating jacket for insulating the cryogenic storage tank 1 or a protective jacket for protecting the cryogenic storage tank 1, or the like, and an access door 8 is provided on the heat-insulating jacket or the protective jacket corresponding to the access opening 5. The shape of the storage housing 7 is also not limited herein.

Figure 5:
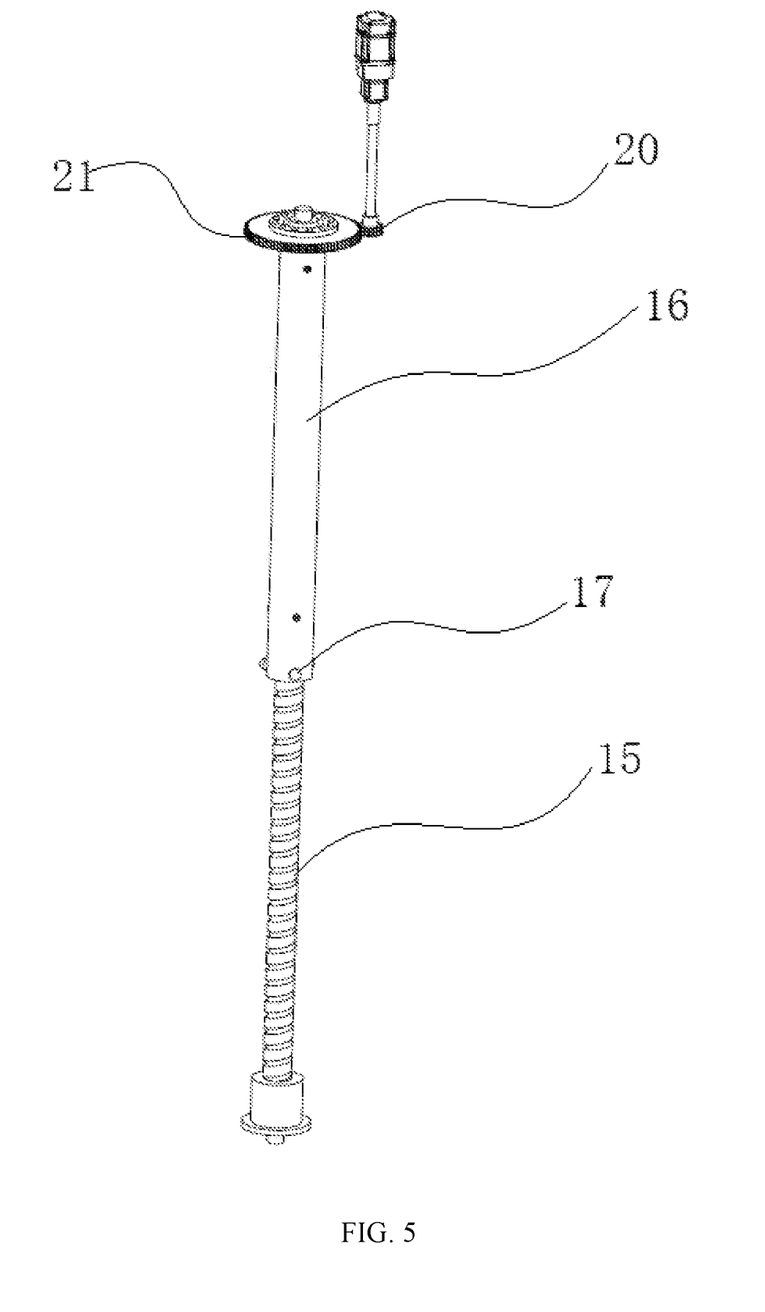
FIG. 5 is a schematic view of a drive assembly.

Taking the liquid nitrogen tank being the cryogenic storage tank 1 as an example, an implementation of the drive assembly 2 is further disclosed. The drive assembly 2 includes a drive motor 9, a transition gear assembly 10, and a drive shaft assembly 11. The drive motor 9 is connected to the transition gear assembly 10, the transition gear assembly 10 is connected to the drive shaft assembly 11, and the drive motor 9 can drive the drive shaft assembly 11 to rotate through the transition gear assembly 10. The rotation storage rack 3 is provided with an operation channel 12 extending through from top to bottom at a center of the circumference, the drive shaft assembly 11 acts in the operation channel 12, and the drive shaft assembly 11 is provided with a drive connection unit 13, a drive receiving unit 14 is provided in the operation channel 12. The drive shaft assembly 11 can act on the drive receiving unit 14 through the drive connecting unit 13 to drive the rotating storage rack 3 to rotate. The cooperation of the drive connecting unit 13 and the drive receiving unit 14 realizes the rotation of the rotating storage rack 3, and thus the drive receiving unit 14 limits the drive connecting unit 13 in the circumferential direction. That is, when the drive connecting unit 13 moves in the circumferential direction, the drive receiving unit 14 is subjected to an opposite circumferential force due to limitation on the drive connecting unit 13 in the circumferential direction, so that the rotating storage rack 3 is also subjected to a circumferential force, and the rotating storage rack 3 rotates. Here, the drive receiving unit 14 does not limit the drive connecting unit 13 in the axial direction.

In a further detailed specific implementation, the drive shaft assembly 11 includes a lead screw 15 and a rotation shaft sleeve 16. The transition gear assembly 10 is connected to the rotation shaft sleeve 16. The rotation shaft sleeve 16 is sleeved at the periphery of the upper half of the lead screw 15, a lower end of the lead screw 15 extends out of the rotation shaft sleeve 16. The periphery of the circumference of the rotation shaft sleeve 16 extends outwards to form at least one guide ball 17, and an inner wall of the operation channel 12 of the rotating storage rack 3 is recessed inwards to form at least one guide groove 18, and the guide ball 17 extends into the guide groove 18. Under the cooperation of the guide ball 17 and the guide groove 18, the rotation shaft sleeve 16 can drive the rotating storage rack 3 to rotate in a circumferential direction. The operation channel 12 of the rotating storage rack 3 is fixedly provided with an inner nut seat 19 at a lower end thereof, and the lower end of the lead screw 15 passes through the operation channel 12 and is threadedly connected to the inner nut seat 19.

The transition gear assembly 10 is connected to the rotation shaft sleeve 16, so that when the drive motor 9 acts on the transition gear assembly 10 to drive the transition gear assembly 10 to operate, the rotation shaft sleeve 16 is driven to rotate. Since the rotation shaft sleeve 16 extends outwards to form the guide ball 17, and the inner wall of the operation channel 12 is recessed inwards to form the guide groove 18, under the cooperation of the guide ball 17 and the guide groove 18, the rotation shaft sleeve 16 can drive the rotating storage rack 3 to rotate in the circumferential direction. When the rotating storage rack 3 rotates, the inner nut seat 19 provided at the lower end of the operation channel 12 is threadedly connected to the lead screw 15 so that the rotating storage rack 3 moves up and down linearly along the lead screw 15.

The provision of the above-mentioned drive shaft assembly 11 and the rotating storage rack 3 enables the rotating storage rack 3 to achieve spiral ascent or rotation in the current space, ensuring the safety of storage or retrieval of the cryopreservation tubes, and improving the access efficiency of biological tissues in the cryopreservation tubes, making the overall size compact, also greatly increasing the storage space.

It should be noted here that the cooperation of the guide ball 17 and the guide groove 18 described above realizes the circumferential movement of the rotating storage rack 3, but it is not limited to the provision of the guide ball 17 and the guide groove 18. For example, a spiral curved guide rail can be recessed in the operation channel 12, and a sliding block that cooperates with the spiral curved guide rail can be provided outside the rotation shaft sleeve 16, so as to realize the spiral ascending or descending of the rotating storage rack.

In a preferred further implementation of this embodiment, the number of the guide balls 17 is three, and the guide balls 17 are provided on the periphery of the rotation shaft sleeve 16 in a circumferential array. The guide grooves 18 are grooves formed on the inner wall of the operation channel 12 in an axial direction, and there are three guide grooves which are in one-to-one correspondence to the guide balls 17. This provision improves the stability, the guide grooves 18 are grooves formed in the axial direction, which ensures that the guide balls 17 are limited by the guide grooves 18 in the circumferential direction, and is not limited in the axial direction, so that the rotating storage rack 3 can move in the axial direction with high stability.

Figure 6:
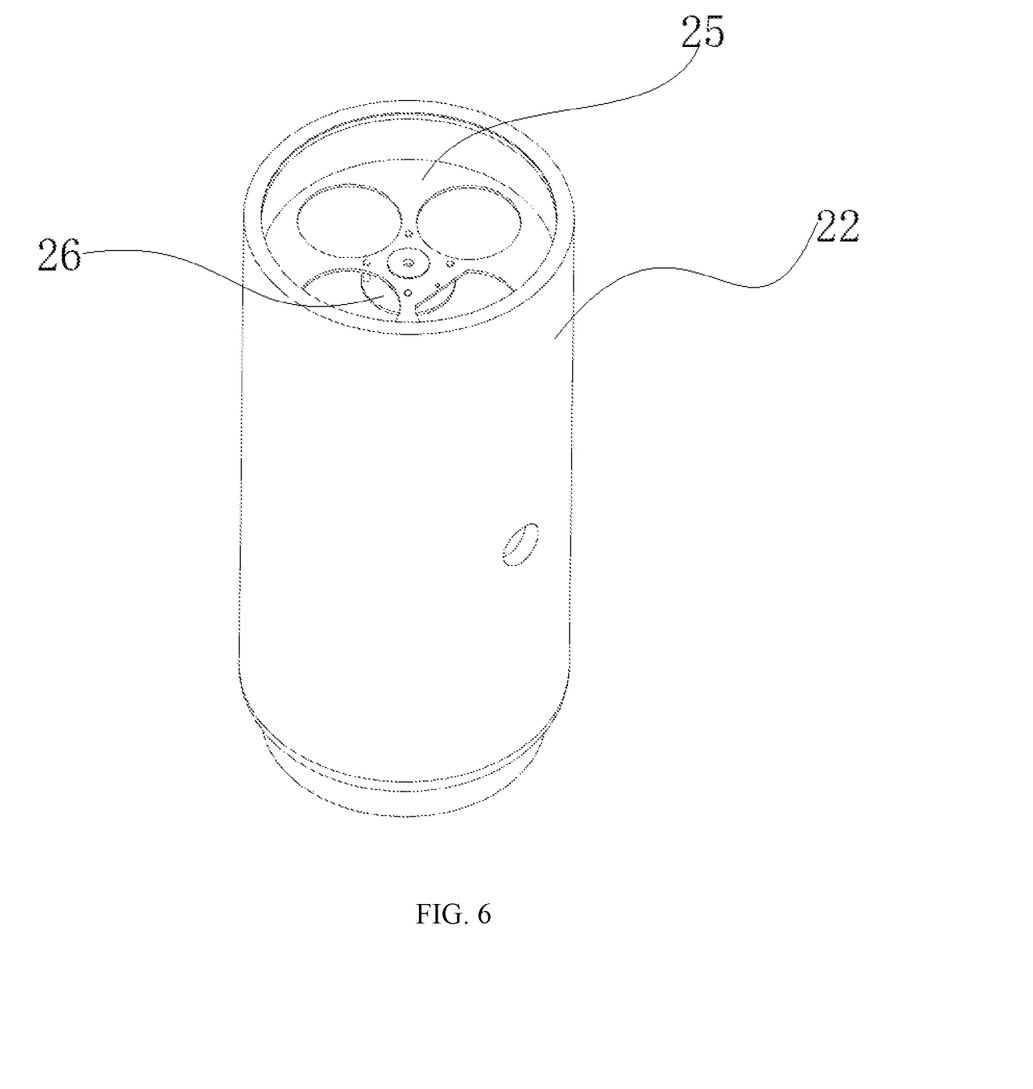
FIG. 6 is a schematic view of a cryogenic storage tank with an upper cover and a sealing cover not shown.

A specific implementation of the transition gear assembly 10 is further disclosed herein. The transition gear assembly 10 includes a driving wheel 20 and a driven wheel 21. The driving wheel 20 is connected to a motor shaft of the drive motor 9, and the driving wheel 20 is in gear meshing connection with the driven wheel 21, and the driven wheel 21 is fixedly disposed on a periphery of an upper end of the rotation shaft sleeve 16. The cryogenic storage tank 1 further includes a tank body 22, an upper cover 23, and a sealing cover 24. The rotating storage rack 3 is disposed in the tank body 22, the sealing cover 24 is sealed on an upper end of the tank body 22, and the upper cover 23 is covered on an upper end surface of the sealing cover 24. A fixed plate 25 is fixedly provided under the sealing cover 24, and a fixed disc 26 is fixedly provided under the fixed plate 25. The driven wheel 21 is disposed between the fixed plate 25 and the fixed disc 26, and the driven wheel 21 is in ball sliding connection with both the fixed plate 25 and the fixed disc 26. The drive motor 9 is disposed above the upper cover 23, the motor shaft of the drive motor 9 sequentially passes through the upper cover 23 and the sealing cover 24 and is connected to the driving wheel 20 in the tank body 22.

The liquid nitrogen tank is sealed by the sealing cover 24 to further ensure the deep cryogenic environment of the liquid nitrogen tank. The drive motor 9 is disposed above the upper cover 23 to ensure that the drive motor 9 will not be affected by the deep cryogenic environment. The driven wheel 21 is in ball sliding connection with both the fixed plate 25 and the fixed disc 26. The ball sliding connection here refers to that, bosses can be extended outwardly from both the upper and lower end surfaces of the driven wheel 21, balls are provided on the bosses, and the balls of the upper end surface boss are in sliding contact with the fixed plate 25, and the balls of the lower end surface boss are in sliding contact with the fixed disc 26. The fixed plate 25 and the fixed disc 26 limit the up-and-down movement of the driven wheel 21, and also provide a support force, but does not limit the circumferential rotation of the driven wheel 21 due to the ball sliding connection, thereby ensuring the stability.

Figure 3:
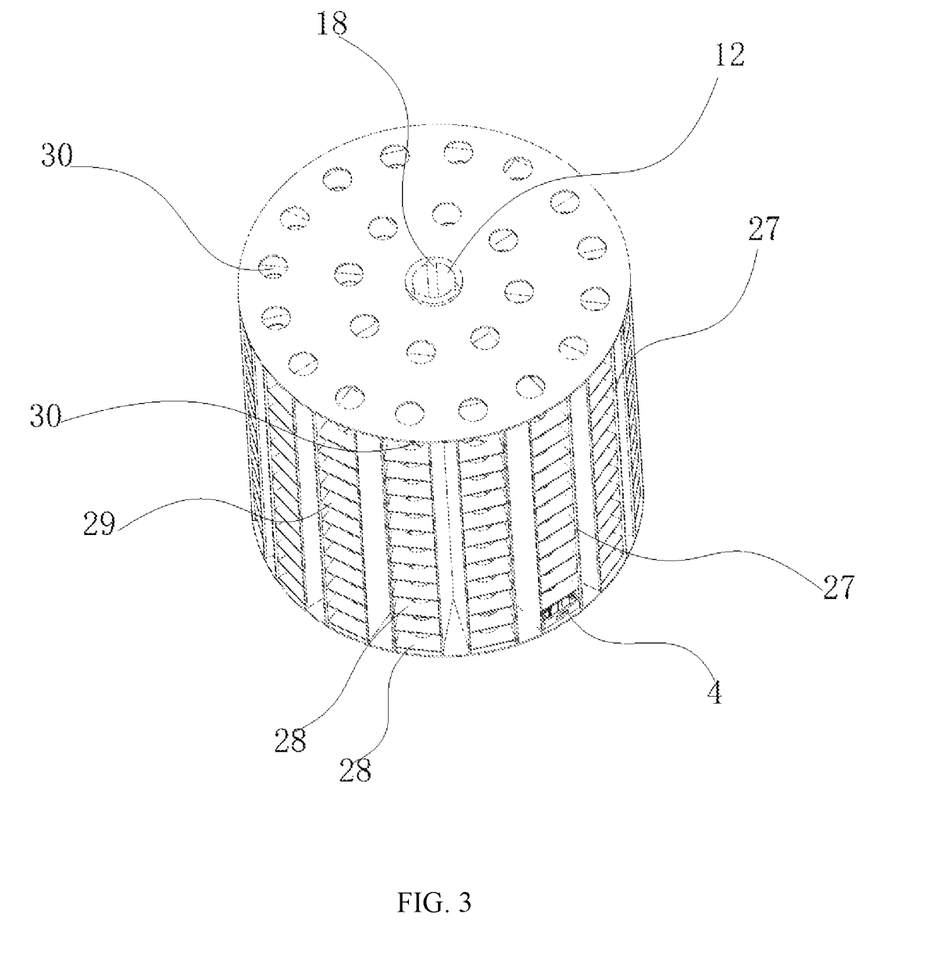
FIG. 3 is a schematic view of a rotating storage rack.
Figure 4:
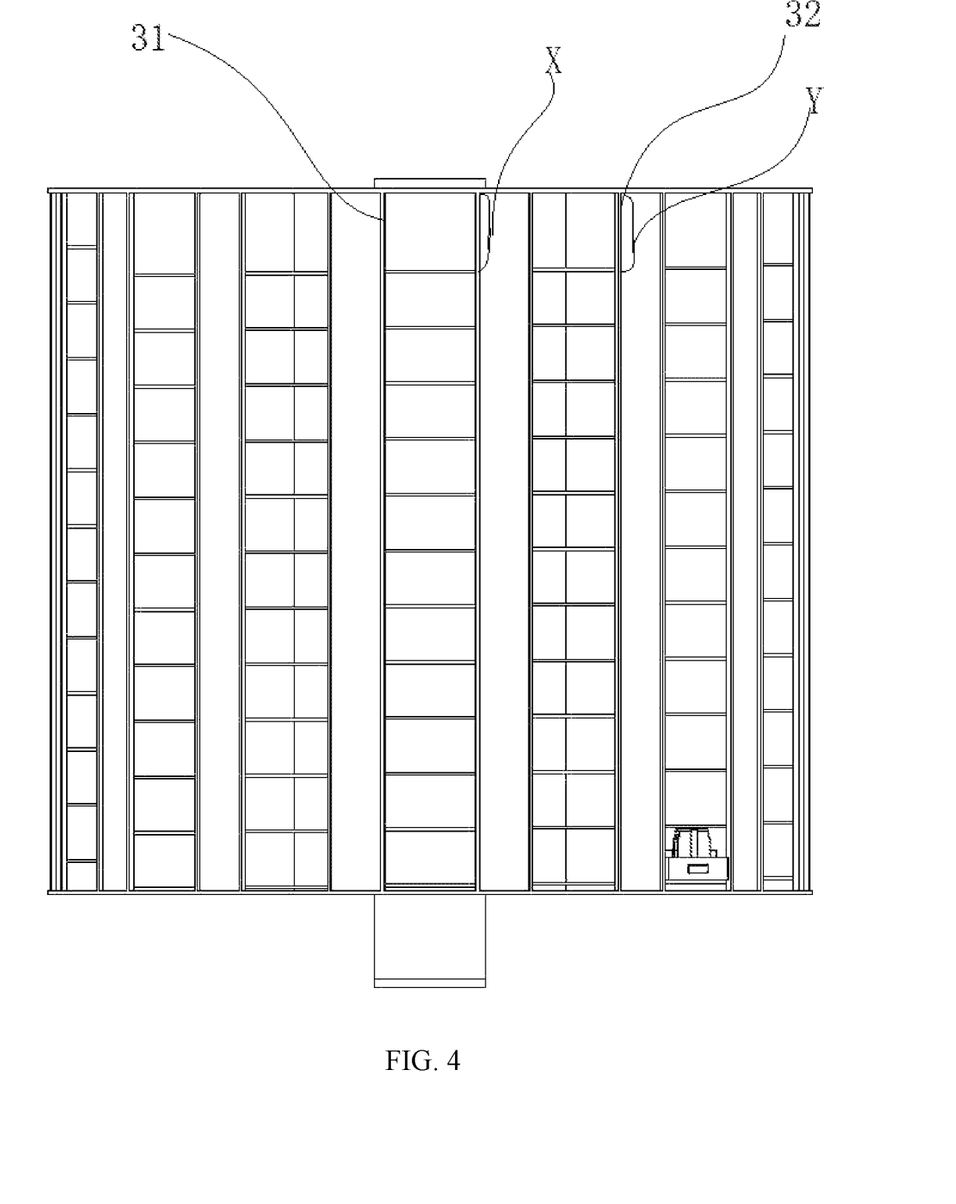
FIG. 4 is a front view of FIG. 3.

This embodiment preferably further discloses the implementation of the rotating storage rack 3, the rotating storage rack 3 is provided by a plurality of rows of sub storage racks 27 distributed in a circumferential direction, and each row of the sub storage racks 27 is divided into a plurality of vertically arranged storage grooves 29 by a plurality of resting plates 28. The shelf boxes 4 are provided in the storage grooves 29. In addition, the rotating storage rack 3 is provided with a plurality of nitrogen introducing holes 30 at the upper end surface and the lower end surface thereof, and each of the resting plates 28 is provided with a nitrogen introducing hole 30. In this way, the sub storage racks 27 are distributed in a circumferential direction, so that the space is fully utilized, ensuring that the overall size is small and exquisite, and the storage capacity is increased. Liquid nitrogen is arranged at the bottom of the liquid nitrogen tank, and nitrogen introducing holes 30 are provided to ensure that nitrogen can fully move upwards, so that the upper part and all directions in the rotating storage rack 3 can be affected by nitrogen, ensuring that the entire liquid nitrogen tank is in a deep cryogenic environment, eliminating the temperature difference between the upper and lower parts of the rotating storage rack 3, and increasing the viability of biological samples.

In a preferred further implementation of this embodiment, the storage grooves 29 between two adjacent rows of sub storage racks 27 are staggered in the axial height, the storage grooves 29 forming the entire rotating storage rack 3 are provided in a spiral arrangement. As shown in FIG. 4, two adjacent sub storage racks: a first sub storage rack 31 and a second sub storage rack 32, a height of the uppermost storage groove 29 of the first sub storage rack 31 is X, and a height of the uppermost storage groove of the second sub storage rack 32 is Y, and X is greater than Y. In this way, the initial heights of the first sub storage rack 31 and the second storage rack 32 are not the same, so that the height of the storage groove of the first storage rack 31 and the height of the storage groove of the second storage rack 32 in the axial direction are staggered. The sub storage racks 27 in the rotating storage rack 3 are sequentially arranged as described above, so that the entire storage groove 27 is provided in a spiral arrangement. In this way, when the rotating storage rack 32 rotates, it is more convenient to correspond to the access opening 5, which is convenient for access.

In a preferred further implementation of this embodiment, the storage housing 7 is provided with an operation hole 33, and the operation hole 33 corresponds to the access opening 5. A transition platform 34 is fixed in the operation hole 33 in an interference fit manner, the transition platform 34 is provided with a transition access through hole 35, the transition access through hole 35 is in communication with the access opening 5. The access door 8 is provided on a side of the transition platform 34 away from the cryogenic storage tank 1. The transition platform 34 is made of a thermal insulation material, and the thermal insulation material is Polyisocyanurate Foam (PIR), Polyurethane Resin (PUR), Expanded polypropylene (EPP), Expanded Polystyrene (EPS), aerogel, or vacuum insulation board.

The provision of the transition platform 34 further provides a stable temperature environment for the liquid nitrogen tank.

In a preferred further implementation of this embodiment, a controller 36 which is electrically connected to the drive assembly 2 and controls the drive assembly 2 is further included.

The access door 8 also includes a controller 36, a door frame 37, an access hole 38, and a door 39. The controller 36 is arranged at the upper part of the door frame 37, and the access hole 38 is formed at the lower part of the door frame 37, and the access hole 38 is in communication with the access opening 5 and the operation hole 33. The controller 36 is electrically connected to the drive assembly 2 and controls the driving of the drive assembly 2.

The controller 36 may include a programmable logic controller (PLC) control board. The PLC control board electrically controls the drive assemblies, and furthermore, electrically controls the drive motor 9. By controlling the drive motor 9, the rotation position of the rotating storage rack 3 is controlled, so that the samples which need to be stored or retrieved are operated.

The sequence of the above embodiments is only for the simplicity of description, and does not represent the advantages and disadvantages of the embodiments.

Finally, it should be noted that the above embodiments are only used to illustrate the technical solutions of the present disclosure, not to limit them. Although the present disclosure has been described in detail with reference to the foregoing embodiments, those of ordinary skills in the art should understand that: the technical solutions recorded in the foregoing embodiments can be modified, or some of the technical features thereof can be equivalently replaced. These modifications or replacements do not cause the essence of the corresponding technical solutions to deviate from the spirit and scope of the technical solutions of the embodiments of the present disclosure.

What is claimed is:

1. A spirally ascending/descending cryogenic storage apparatus, comprising a cryogenic storage tank, a temperature in the cryogenic storage tank being continuously maintained in a certain deep cryogenic range;
   the cryogenic storage tank being provided with a drive assembly and a rotating storage rack therein, the rotating storage rack being capable of storing a plurality of shelf boxes in a circumferential direction; the drive assembly being capable of driving the rotating storage rack to spirally ascend or spirally descend in the cryogenic storage tank;
   the cryogenic storage tank being provided with an access opening, the plurality of shelf boxes being capable of moving to a position corresponding to the access opening along with a movement of the rotating storage rack;
   the cryogenic storage tank being a liquid nitrogen tank, and liquid nitrogen being provided at a bottom in the liquid nitrogen tank.

2. The spirally ascending/descending cryogenic storage apparatus according to claim 1, further comprising a storage housing, wherein the cryogenic storage tank is disposed inside the storage housing, the storage housing is provided with an access door, the access door corresponds to the access opening.

3. The spirally ascending/descending cryogenic storage apparatus according to claim 1, wherein the drive assembly comprises a drive motor, a transition gear assembly, and a drive shaft assembly; the drive motor is connected to the transition gear assembly, the transition gear assembly is connected to the drive shaft assembly, the drive motor is capable of driving the drive shaft assembly to rotate through the transition gear assembly; the rotating storage rack is provided with an operation channel extending through from top to bottom at a center of a circumference thereof, the drive shaft assembly acts in the operation channel, and the drive shaft assembly is provided with a drive connecting unit, and a drive receiving unit is provided in the operation channel, the drive shaft assembly is capable of driving the rotating storage rack to rotate through the drive connecting unit acting on the drive receiving unit.

4. The spirally ascending/descending cryogenic storage apparatus according to claim 3, wherein the drive shaft assembly comprises a lead screw and a rotation shaft sleeve, the transition gear assembly is connected to the rotation shaft sleeve; the rotation shaft sleeve is sleeved on a periphery of an upper half of the lead screw, and a lower end of the lead screw extends out of the rotation shaft sleeve;
   a periphery of a circumference of the rotation shaft sleeve extends outwards to form at least one guide ball, an inner wall of the operation channel of the rotating storage rack is recessed inwards to form at least one guide groove, the guide ball extends into the guide groove; under a cooperation of the guide ball and the guide groove, the rotation shaft sleeve is capable of driving the rotating storage rack to rotate in a circumferential direction;
   the operation channel of the rotating storage rack is fixedly provided with an inner nut seat at a lower end thereof, the lower end of the lead screw passes through the operation channel and is threadedly connected to the inner nut seat.

5. The spirally ascending/descending cryogenic storage apparatus according to claim 4, wherein there are three guide balls, and the guide balls are provided on the periphery of the rotation shaft sleeve in a circumferential array;
   the guide grooves are formed on the inner wall of the operation channel in an axial direction, and there are three guide grooves, the guide grooves are in one-to-one correspondence to the guide balls.

6. The spirally ascending/descending cryogenic storage apparatus according to claim 4, wherein the transition gear assembly comprises a driving wheel and a driven wheel;
   the driving wheel is connected to a motor shaft of the drive motor, the driving wheel is in gear meshing connection with the driven wheel, the driven wheel is fixedly disposed on a periphery of an upper end of the rotation shaft sleeve.

7. The spirally ascending/descending cryogenic storage apparatus according to claim 6, wherein the cryogenic storage tank further comprises a tank body, an upper cover, and a sealing cover; the rotating storage rack is disposed in the tank body, the sealing cover is sealed on an upper end of the tank body, the upper cover is covered on an upper end surface of the sealing cover;
   a fixed plate is fixedly provided under the sealing cover, a fixed disc is fixedly provided under the fixed plate, the driven wheel is disposed between the fixed plate and the fixed disc, and the driven wheel is in ball sliding connection with both the fixed plate and the fixed disc;
   the drive motor is disposed above the upper cover, the motor shaft of the drive motor sequentially passes through the upper cover and the sealing cover and is connected to the driving wheel in the tank body.

8. The spirally ascending/descending cryogenic storage apparatus according to claim 1, wherein the rotating storage rack is provided by a plurality of rows of sub storage racks distributed in a circumferential direction, and each row of the sub storage racks is divided into a plurality of vertically arranged storage grooves by a plurality of resting plates; the shelf boxes are disposed in the storage grooves;
   the rotating storage rack is provided with a plurality of nitrogen introducing holes at an upper end surface and a lower end surface thereof, and each of the resting plates is provided with a nitrogen introducing hole.

9. The spirally ascending/descending cryogenic storage apparatus according to claim 8, wherein the storage grooves between two adjacent rows of the sub storage racks are staggered in an axial height, the storage grooves forming the entire rotating storage rack are provided in a spiral arrangement.

10. The spirally ascending/descending cryogenic storage apparatus according to claim 2, wherein the storage housing is provided with an operation hole, the operation hole corresponds to the access opening;
    a transition platform is fixed in the operation hole in an interference fit manner, the transition platform is provided with a transition access through hole, the transition access through hole is in communication with the access opening;
    the access door is disposed on a side of the transition platform away from the cryogenic storage tank.

11. The spirally ascending/descending cryogenic storage apparatus according to claim 10, wherein the transition platform is made of a thermal insulation material, and the thermal insulation material is polyisocyanurate foam (PIR), polyurethane resin (PUR), expanded polypropylene (EPP), expanded polystyrene (EPS), aerogel, or vacuum insulation board.

12. The spirally ascending/descending cryogenic storage apparatus according to claim 1, further comprising a controller, the controller is electrically connected to the drive assembly and controls the drive assembly.

13. The spirally ascending/descending cryogenic storage apparatus according to claim 10, wherein the access door further comprises a controller, a door frame, an access hole, and a door, the door frame is provided with the controller at an upper part thereof, and the door frame is provided with the access hole at a lower part thereof, the access hole is in communication the access opening and the operation hole; the controller is electrically connected to the drive assembly, and controls the driving of the drive assembly.

* * * * *